(12) United States Patent
Steinmeyer et al.

(10) Patent No.: US 8,386,016 B2
(45) Date of Patent: Feb. 26, 2013

(54) METHOD AND DEVICE TO DETERMINE A POSITION SHIFT OF A FOCAL AREA

(75) Inventors: Florian Steinmeyer, Herzogenaurach (DE); Michael Zwanger, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 301 days.

(21) Appl. No.: 12/366,772

(22) Filed: Feb. 6, 2009

(65) Prior Publication Data

US 2009/0203987 A1 Aug. 13, 2009

(30) Foreign Application Priority Data

Feb. 7, 2008 (DE) .......................... 10 2008 007 968

(51) Int. Cl.
*A61B 5/05* (2006.01)
(52) U.S. Cl. ......... 600/412; 600/407; 600/410; 600/411
(58) Field of Classification Search ................ 600/407, 600/410, 411, 412, 425; 601/3
See application file for complete search history.

(56) References Cited

U.S. PATENT DOCUMENTS

| 5,590,653 | A | | 1/1997 | Aida et al. | |
| 5,722,411 | A | * | 3/1998 | Suzuki et al. | ................. 600/439 |
| 5,897,495 | A | | 4/1999 | Aida et al. | |
| 6,076,004 | A | * | 6/2000 | Kanayama et al. | ........... 600/410 |
| 2006/0036156 | A1 | | 2/2006 | Lachaine et al. | |
| 2006/0293598 | A1 | | 12/2006 | Fraser | |

* cited by examiner

*Primary Examiner* — Tse Chen
*Assistant Examiner* — Jason Ip
(74) *Attorney, Agent, or Firm* — Schiff Hardin LLP

(57) ABSTRACT

In a method and device for determination of a position shift, first image data of a body region of a treatment-positioned patient that contain derivable temperature information are acquired. A focal area in the body region is determined, and the focus of a hyperthermia applicator can be aligned on the focal area. Second image data of the body region of the treatment-positioned patient that contain derivable temperature information are acquired, and a position shift of the focal area is determined by a comparison of the second image data with the first image data.

16 Claims, 1 Drawing Sheet

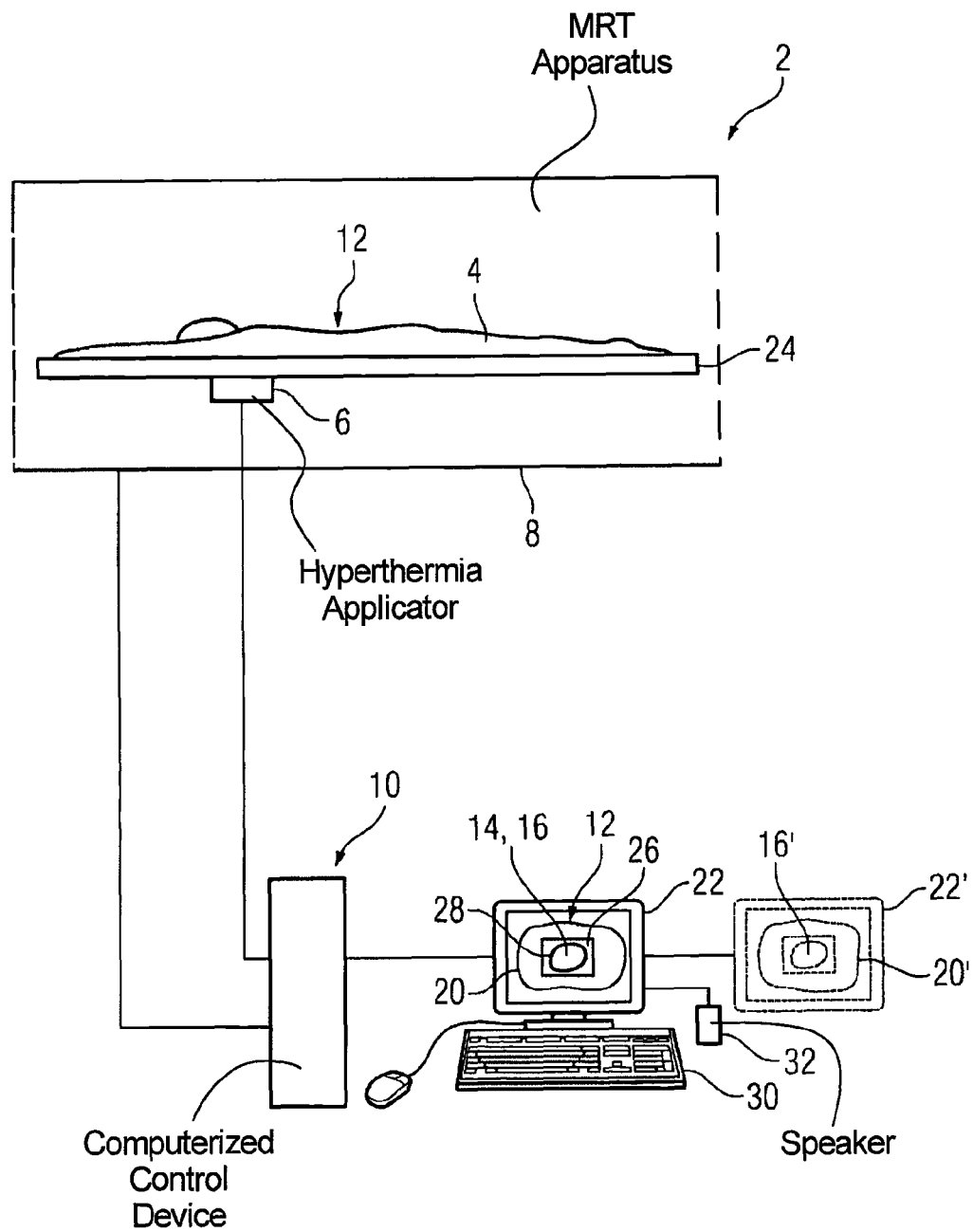

METHOD AND DEVICE TO DETERMINE A POSITION SHIFT OF A FOCAL AREA

BACKGROUND OF THE INVENTION

1. Field of the Invention

The present invention concerns a method to determine a position shift of a focal area as well as a corresponding device. The invention in particular concerns such a method and device in the field of hyperthermia application.

2. Description of the Prior Art

Hyperthermic treatment of tumor tissue has attracted increasing interest in medical cancer treatment. In such a hyperthermic treatment of tumor tissue (also called hyperthermia) the tumor tissue is heated to temperatures of over 42.5° C. Hyperthermia in cancer treatment is frequently used as a measure supporting radiation and/or chemotherapy. Hyperthermic treatment of tumor cells in which these cells are heated to temperatures of, for example, above 60° C., is often referred to as heat therapy; such treatment generally leads to a heat-induced destruction of the tumor cells.

In hyperthermia, differentiation is made between whole-body hyperthermia and local hyperthermia. Whole-body hyperthermia can occasionally lead to severe stress on the cardiovascular system of the patient.

By contrast, local hyperthermia is intended to overheat only a narrowly defined region, for example only the tumor tissue. Ultrasonic waves, infrared rays, microwaves or laser beams which are normally focused on the area to be heated (thus the tumor tissue, for example) using a corresponding hyperthermia applicator in order to achieve an overheating (in particular a local overheating), whereby the tumor tissue is damaged or entirely destroyed by the overheating. This is also referred to as thermal ablation or thermoablation.

In order to guarantee the effectiveness of such a local treatment, and in order to avoid the destruction of healthy tissue, it is necessary to know the position of the tumor precisely in order to ensure the precise alignment of the focus of the hyperthermia applicator relative to the focal area to be heated in a subsequent treatment.

For this purpose, in DE 694 28 146 T2 an ultrasound device is disclosed in which a patient is placed on a treatment table of the device during a hyperthermia treatment so that the tumor to be heated is localized over a treatment opening located in the treatment table. An ultrasonic wave applicator is rigidly attached below the treatment opening, so the position of the ultrasonic wave applicator is fixed relative to the area to be heated. A shift of the ultrasonic wave focus relative to the area to be heated can nevertheless occur, for example as a result of a movement of the patient (for example a breathing movement), and therefore the risk of damage to healthy tissue cannot be entirely precluded.

SUMMARY OF THE INVENTION

An object of the present the invention is to provide a method to determine a position shift of a focal area. An additional object is to provide a corresponding device.

This object is achieved in accordance with the invention by a method wherein first image data of a body region of a treatment-positioned patient are acquired that contain derivable temperature information. A focal area in the body region is determined, so the focus of a hyperthermia applicator can be aligned relative to the focal area. Second image data of the body region of the treatment-positioned patient that contain derivable temperature information are then acquired, and a position shift of the focal area is determined by a comparison of the second image data with the first image data.

The invention begins from the general consideration that, for an effective hyperthermic treatment (in particular a thermal ablation) of a tumor tissue, for example, it is necessary to precisely know the position of the tumor in order to align the focus of the hyperthermia applicator precisely on an area to be heated in the subsequent treatment, thus on a focal area in a body region of the patient. For example, the focal area can be an area of a tumor tissue.

The invention is based on the observation that, the potential exists for the hyperthermia applicator to damage a body tissue due to overheating (for example also the danger of damaging healthy tissue, for example body tissue adjoining a tumor tissue) when a position shift of the focal area relative to the focus of the hyperthermia applicator is not posted. Given such an oversight, for example, it is not possible for a treating physician to avoid damage to healthy tissue by a corresponding reaction (for example by refraining from starting up the hyperthermia applicator).

Image data containing temperature information as are used to monitor a hyperthermia application are normally optimized for visualization of a temperature of the body region in the form of a thermometry image. Due to this, a presentation of such image data frequently shows anatomical details only in a very fuzzy and noisy manner, such that it is not possible for (for example) a physician to reliably recognize a position change of a patient using anatomical or other optical landmarks in order to conclude from this a position shift of the focal area.

The invention is based on the insight that the image data containing temperature information can nevertheless be used to detect a position change. For this purpose, a position shift of the focal area is determined by an image data comparison. In this image data comparison, second image data containing temperature information are compared with first image data containing temperature information, meaning that an image data set acquired at a later point in time is compared with an image data set acquired earlier. First image data containing temperature information are basically acquired from a body region of the patient immediately after an appropriate positioning of the patient and obtaining a reference data set. By means of such a reference data set it is possible to establish a shift of the focal area (for example as a result of a slight movement of the patient) automatically, and thus essentially without time delay, as well as without the necessity of an interaction of a user (for example a physician) using a deviation in the subsequently acquired image data. A high resolution of anatomical details is not required for this.

The image data are generated with the image acquisition apparatus present for a hyperthermia application.

The position shift is in particular determined automatically and realized as a displacement vector or a corresponding matrix. For example, the time curve of the focal area can be recorded (detected) and evaluated. Alternatively, the position shift, for example the displacement vectors representing the position shift, can be stored. This affords the possibility to generate a "displacement profile" from temporally independent measurements which, for example, also allows a conclusion of how frequently a position shift occurs and how large it is in each case. It is also possible to determine from this an average position shift, from which an expected value for a position shift can be derived if necessary.

The image data are frequently 2D image data or 3D image data that are acquired from a body region of the treatment-positioned patient. The body region is or encompassed the focal area (for example a tumor tissue).

The image data contain temperature information. For this purpose, the image data are acquired, for example, by magnetic resonance tomography (MRT). The different temperature-dependent, "MRT-relevant" parameters (the temperature dependency of the diffusion coefficients of water is an example) allow a non-invasive, spatially resolved temperature measurement. It is thereby possible to determine a temperature of the body region using the image data and to present it in the form of a thermometry image. Such an (in particular immediate) visualization of the temperature of the body region affords the possibility for the physician to assess, if necessary, the course of a hyperthermic treatment, in particular a thermal ablation (for example of a tumor tissue), using the thermometry image.

The focus of the hyperthermia applicator can be aligned relative to the focal area. Upon start-up of the hyperthermia applicator, the focal area may be overheated by means of the hyperthermia applicator, which (as already noted) can occur in a tumor treatment. The hyperthermia applicator can be, for example, a focusable ultrasound applicator, as a laser source or as a microwave applicator.

If a position shift is determined to have occurred, a fault is appropriately established in accordance with the invention. This affords the possibility for a measure to be taken (for example, refraining from starting up the hyperthermia applicator) as a reaction to the position shift of the focal area or, for example, to update (track) the applicator corresponding to the shift.

If the distance of the position-shifted focal area from the determined focal area is determined, this distance can be compared with a predetermined threshold and, given an overrun of the threshold by the distance, the fault is established. Expressed in other words, this means that a "tolerance range" is predetermined by the threshold, in the scope of which a shift of the focal area is tolerable and is tolerated without a fault being established. The threshold can be predetermined as a fixed value, or can be varied from measurement to measurement, for example. In particular, it is also possible to predetermine the threshold differently depending on a considered displacement direction, meaning, for example, that the threshold for a displacement in the x-direction can be different than for a displacement in the y- or z-direction. The threshold can be automatically provided by a corresponding control device. Alternatively, the threshold is set (for example by a physician) through a user interface by means of a mouse pointer or by means of a keyboard input, which allows very simple operability.

In an embodiment, a warning signal is emitted given an established fault. The warning signal can be both acoustic and optical in nature. With the warning signal it is possible, for example, to unambiguously and urgently indicate a position shift of the focal area to a physician so that he can correspondingly react to this if necessary. An acoustic warning signal is particularly suitable for use in this context since the perception thereof (by a physician, for example) is independent of the viewing direction.

In a preferred embodiment of the invention, given an established fault, start-up of the hyperthermia applicator is prevented. Given a treatment that is already running, a continued operation of the hyperthermia applicator is in particular prevented. It is thereby possible to prevent damage to healthy tissue in any case—even if the physician has not perceived the warning signal, for example—by preventing the beginning of the hyperthermic treatment, or by terminating a treatment that has already started, as necessary.

The focus of the hyperthermia applicator is advantageously adjusted to the displaced position of the focal area. It is thereby ensured that no danger of damage to healthy tissue arises from a position shift of the focal area in the event of a start-up of the hyperthermia applicator.

In another embodiment of the invention, a tissue region of the body region that encompasses the focal area is determined and a position shift of the focal area is determined by a comparison of the second image data representing the tissue region with the first image data representing the tissue region. For example, the determined tissue region includes the tumor tissue or an organ, or is entirely predetermined by the tumor tissue or the organ. In this embodiment of the invention, the complete data set of the first image data and that of the second image data are not compared with one another. Rather, the comparison occurs using a respective reduced data set of the addressed image data. The data quantity to be processed is thereby significantly reduced, so a computer with a lower computation capacity can be used, for example. Additionally, movements that ensue outside of the tissue region and that typically have no influence on the position of the focal area are thereby disregarded.

The position shift is advantageously determined by means of a cross-correlation of the image data. A cross-correlation can be done, for example, by comparing a time series is compared with another, time-offset time series, for example comparing x(t) with y(t+shift). Here the first image data are compared with the second image data that are acquired later in time. A known and quick algorithm used for the image data comparison by means of a cross-correlation. For the execution of this algorithm, existing software can be used, for example.

The position shift is advantageously determined with incorporation of image sharpness information of the image data. "Image sharpness" means a criterion that can be viewed and measured at edges in the image. The more abrupt the transition from dark to light in an image presentation, the greater the image sharpness. In this embodiment of the invention, the fact that an abrupt brightness jump is normally to be observed (for example at a boundary of a tumor tissue or an organ) is utilized. It is thereby possible to identify the boundary (for example of a tumor tissue) using the image sharpness information. The image sharpness information can also be utilized, for example, in order to modulate the image data by means of an "edge filtering" such that, for example, the boundary of the tumor tissue is intensified relative to a surrounding body tissue so that this boundary is made to be sharper (in presentation terms). The detection of a position shift of the focal area, for example by means of a cross-correlation, is thereby additionally significantly facilitated.

A device is achieved according to the invention to determine a position shift of a focal area accordingly has a hyperthermia applicator whose focus can be aligned, an image acquisition apparatus, and a control device. The image acquisition apparatus is configured to acquire first and second image data of a body region of a real positioned patient that respectively contain temperature information. The control device is configured to determine a focal area in the body region, to control an alignment of the focus of the hyperthermia applicator relative to the focal area, and to determine a position shift of the focal area by a comparison of the second image data with the first image data.

The advantages described above for the method are applicable to the device.

As previously described, it is particularly advantageous to design the image acquisition apparatus as an MRT apparatus since both the acquisition of the image data containing temperature information and the image acquisition (frequently designed to be high-resolution) to determine the focal area are possible by means of the MRT apparatus. For example, a relocation of the patient can thereby be avoided, which in particular is advantageous with regard to the avoidance of a position change of the patient between the different acquisitions.

The control device is provided as a computer or is realized on a computer via software, for example.

For a processing the image data, the control device is appropriately connected in terms of data with the image acquisition apparatus.

To control the hyperthermia applicator, the control device is connected with the corresponding hyperthermia applicator.

For emission of a warning signal, the control device can (for example) have a signaling device or be connected with such a signaling device via an interface.

The control device uses a suitable data processing program, for example for a determination of the focal area in the body region encompassed by the means of the image data, as well as possibly for a determination of the tissue region comprising the focal area.

The control device can also include a user interface or be connected with a user interface. For example, via such a user interface it is possible for a physician to set a threshold manually by means of a mouse pointer or a keyboard input.

BRIEF DESCRIPTION OF THE DRAWING

The single FIGURE schematically illustrates an embodiment of a device to determine a position shift of a focal area in a patient, in accordance with the present invention, that implements the method in accordance with the invention.

DESCRIPTION OF THE PREFERRED EMBODIMENTS

The FIGURE shows a device 2 to determine a position shift of a focal area. A hyperthermic treatment of a tumor tissue of a patient 4 can be implemented with the device 2.

In particular, a method workflow of an embodiment of the method according to the invention should be explained using the representation.

The presented device 2 has a hyperthermia applicator 6, an image acquisition apparatus executed as a magnetic resonance tomography apparatus 8 (MRT apparatus) and a computer as a control device 10.

High-resolution image exposures of a dorsal body region 12 of the real positioned patient 4 are initially acquired by means of the MRT apparatus 8. The corresponding image exposures are 2D image exposures which are acquired in a scan operation of the MRT apparatus 8. As an alternative, it is also possible to acquire high-resolution 3D image data of the body region 12. The 2D image exposures deliver a very detailed depiction of anatomical features of the body region 12 so that the precise position of a tumor tissue 14 located in the body region 12 is apparent from the high-resolution image exposure (not shown here). Based on the position of the tumor tissue 14, the control device 10 determines a focal area 16 in the body region 12 as is required for (for example) a subsequent hyperthermic treatment of the tumor tissue 14. The focal area 16 here essentially coincides with the area of the tumor tissue 14. To determine the focal area 16, the control device 10 comprises a corresponding image processing software with whose help the physician predetermines the therapy volume.

The hyperthermia applicator 6 is executed as an ultrasonic applicator that can be aligned and can be controlled by the control device 10 with regard to an alignment of its focus on the focal area 16.

In the event of a start-up of the hyperthermia applicator 6, in particular given an aligned focus, it is possible to achieve a targeted overheating of the focal area 16 and therefore of the tumor tissue 14 in order to achieve a destruction of the tumor tissue 14, for example.

To achieve overheating, the hyperthermia applicator 6 generates intense ultrasonic energy. In order to enable an alignment of the intense ultrasonic waves at the focal area 16 of the patient 4, the hyperthermia applicator 6 is mounted below the patient 4 on a treatment table 24 of the MRT apparatus 8. In order to enable a low-attenuation propagation of the ultrasonic waves, a water bottle or bath (not visible) is located in direct contact between the patient 4 and the hyperthermia applicator 6.

First and second image data of the body region 12 of the patient 4 that contain temperature information are now acquired by means of the MRT apparatus 8, wherein the second image data are acquired chronologically after the first image data. The use of the MRT apparatus 8 allows the image data containing temperature information to be acquired with the same apparatus as the high-resolution image exposures.

The use of the MRT apparatus 8 allows the various exposures to be obtained without a transfer of the patient 4 being necessary, which is particularly advantageous with regard to avoiding a position shift of the patient 4.

Due to the temperature dependency of various MRT-relevant parameters, the acquired image data contain temperature information. For example, the temperature information can be extracted from the phase information of the measurement signal. Using the image data a thermometry image 20 of the body region 12 is determined and presented on a monitor 22, as shown sketched in FIG. 1. The thermometry image 20 affords the possibility to the physician to detect (dissociated from the therapy) a temperature increase in the acquired body region 12 and, for example, to assess the course of an implemented hyperthermic treatment of the tumor tissue 14.

Both the thermometry image 20 acquired from the first image data and the thermometry image 20' acquired from the second image data are presented in sketches in the FIGURE.

In order to illustrate the time sequence, two monitors 22, 22' are presented in FIG. 1, wherein the dashed presentation of the one monitor 22' indicates that the presented thermometry image 20' was acquired in the past using the first image data. The first image data or, respectively, the thermometry image 20' obtained from them represent/represents the "unshifted" position of the focal area.

As noted above, upon a start-up of the hyperthermia applicator 6 it is possible (for example in the framework of a hyperthermic treatment of the tumor tissue 14) to bring about a targeted overheating of the focal area 16 and therefore of the tumor tissue 14, which results (for example) in a destruction of the tumor tissue 14. Due to the inherent potential capability of the hyperthermia applicator 6 to damage a body tissue by overheating, the danger also exists (for example) of damage to healthy tissue (for example to body tissue adjoining the tumor tissue 14), in particular when a position shift of the focal area 16 relative to the focus of the hyperthermia applicator 6 is overlooked. In order to reliably avoid an oversight of a position shift of the focal area 16, the device 2 implements an automated image data comparison using the first and the second image data and determines a position shift of the focal area 16 based thereon.

At this point it is again noted that the first image data represent the "unshifted" initial position of the focal area 16'. It is thereby possible to use the first image data as a manner of reference data set to determine a position shift of the focal area 16.

To determine the position shift, the control device 10 (in general terms) compares an image data set that is acquired later with the reference data set. Here, this means that the second image data are compared with the first image data.

The results of the image data comparison are evaluated by the control unit 10 with regard to a position shift of the focal area 16 so that a shift of the focal area 16 can be detected automatically, and thus essentially without a time delay, as well as without the necessity of an interaction of a user.

In the shown embodiment, the control device 10 does not implement the image data comparison with the respective complete data set of the first and second image data that is acquired by the MRT apparatus 8; rather, a reduced data set of the respective image data is used for this comparison.

The reduced data set relative to the data of the first and second image data that represents to a tissue region 26 that defines a narrow region around the tumor tissue 14. The corresponding tissue region 26 is thereby established by a physician using the high resolution image exposures, for example.

With the implementation of the data comparison using the reduced data sets, the data quantity to be processed is significantly reduced, and movements that occur outside of the tissue region 26 and that essentially have no influence on the position of the focal area 16 are disregarded.

Before the comparison of the reduced image data sets with one another, the control device 10 filters the image data such that the boundary 28 of the tumor tissue 14 emerges sharper relative to the remaining tissue region 26. Such a filtering is also known as "edge filtering". The fact that normally an abrupt brightness jump is to be observed at the boundary 28 of a tumor tissue 14 is thereby utilized. By the "edge filtering" the image data are modulated so that the boundary 28 of the tumor tissue 14 (and therefore of the focal area 16) can be easily identified, which is reasonable in the framework of a detection of a position shift of the focal area 16. For example, the image data can additionally be processed by means of a weighting function (for example in the form of a Gaussian filter) to suppress artifacts.

The control device 10 subjects the reduced and edge-filtered data set of the second image data to a comparison with the likewise reduced and edge-filtered reference data set of the first image data.

The control device 10 executes the control device 10 by means of a cross-correlation of the corresponding image data. A known and fast algorithm (for the execution of which the control device 10 comprises a corresponding software) is resorted to for the image data comparison by means of a cross-correlation.

The control device 10 identifies the position shift of the focal area 16 from the comparison.

Given a determined position shift of the focal area 16, the control device 10 determines a distance of the position-shifted focal area 16 relative to the "unshifted" focal area 16'. The "unshifted" focal area 16' is derived from the reference data set of the first image data. The control device 10 compares the determined distance of the position-shifted focal area 16 from the "unshifted" focal area 16' with a threshold and, upon the distance exceeding the threshold, the control device establishes a fault.

The threshold here was previously input by a physician via a keyboard 30.

Given an established fault, the control device 10 executed as a computer emits a warning signal. For this the control device 10 (respectively the computer) has a speaker 32. For example, a physician is urgently notified of a position shift of the focal area 16 via the acoustic warning signal.

In addition to the emission of the warning signal, the control device 10 disconnects the hyperthermia applicator 6 from a power supply so that its start-up (or, respectively, its continued operation) is prevented. It is thereby possible to prevent damage to healthy tissue in any case, even if the physician has (for example) not perceived the warning signal, in particular in that the beginning of a hyperthermia treatment is prevented.

As an additional measure the control device 10 can control the hyperthermia applicator 6 for an adaptation of its focus to the displaced position of the focal area 16. It is thereby ensured that no danger of damage to healthy tissue arises even in the event of a start-up of the hyperthermia applicator 6.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining a position shift of an area in an examination subject, comprising the steps of:
   acquiring first magnetic resonance (MR) image data from a body region of a patient positioned for hyperthermia treatment in an MR imaging apparatus by operating said MR imaging apparatus with an operating sequence that causes said first MR image data to be optimized to embody derivable temperature information and, as a consequence, causes said first MR image data to embody imprecise representations of anatomical structures;
   supplying said first MR image data to a computerized processor and, in said processor, from said first MR image data, determining an area to be treated in said body region by said hyperthermia treatment;
   from said processor, controlling alignment of a focus of a hyperthermia applicator relative to a position of said area to be treated in order to place said focus within said area to be treated;
   operating said MR imaging apparatus with said operating sequence to acquire second MR image data, also embodying derivable temperature information and imprecise representations of anatomical structures, from said body region of said patient;
   in said processor, comparing said second MR image data with said first MR image data to identify if a position shift of said area to be heated has occurred after placing said focus within said area to be treated by recording and evaluating a time curve of said position of said area to be treated, and, if so, identifying, from said time curve, a distance of the position-shifted area to be treated from the location of the area to be treated represented by said first image data, comparing said distance with a predetermined threshold, and generating a signal indicative of a fault if said distance exceeds said threshold; and
   deriving temperature information, as derived temperature information, from the derivable temperature information embodied in at least one of said first and second MR images, and monitoring said hyperthermia treatment using said derived temperature information.

2. A method as claimed in claim 1 comprising, in said processor, evaluating a characteristic of said position shift also and emitting said signal indicative of a fault dependent on said characteristic.

3. A method as claimed in claim 1 comprising emitting a humanly-perceptible warning signal upon determination of said fault.

4. A method as claimed in claim 1 comprising automatically precluding start-up of said hyperthermia applicator if said fault is determined to be present.

5. A method as claimed in claim 1 comprising adapting a position of the focus of said hyperthermia applicator to the position-shifted location of the area to be treated.

6. A method as claimed in claim 1 comprising determining a tissue region in said body region that comprises said area to be treated, and determining said position shift by comparing only data in said second image data representing said tissue region with only data in said first image data representing said tissue region.

7. A method as claimed in claim 1 comprising determining said position shift by cross-correlating said first and second image data.

8. A method as claimed in claim 1 comprising analyzing said first and second image data to identify image sharpness information in each of said first and second image data, and determining said position shift dependent on the image sharpness information respectively in said first and second image data.

9. A device for determining a position shift of an area in an examination subject, comprising:

- a magnetic resonance (MR) imaging apparatus configured to acquire first MR image data from a body region of a patient positioned for hyperthermia treatment in said MR imaging apparatus, by operation with an operating sequence that causes said first MR image data to be optimized to embody and, as a consequence, cause said first MR image data to embody imprecise representations of anatomical structures;
- a processor configured to determine, from said first MR image data, an area to be treated in said body region by said hyperthermia treatment;
- a hyperthermia applicator having a focus, said focus being adjustable so as to be aligned relative to a position of said area to be treated;
- a control unit configured to position said focus of said hyperthermia applicator to cause said focus to be within said area to be treated;
- said MR imaging apparatus also being configured to acquire second image data, also embodying derivable temperature information and imprecise representations of anatomical structures, from said body region of said patient;
- said processor being configured to compare said second MR image data with said first MR image data to identify if a position shift of said area to be treated has occurred after placement of said focus within said area to be treated by recording and evaluating a time curve of said position of said area to be treated and, if so, to identify a distance of the position-shifted area to be treated from the location of the area to be treated represented by said first image data, compare said distance with a predetermined threshold, and generate a signal indicative of a fault if said distance exceeds said threshold; and
- said processor being configured to derive temperature information, as derived temperature information, from the derivable temperature information embodied in at least one of said first and second MR images, and to monitor said hyperthermia treatment using said derived temperature information.

10. A device as claimed in claim 9 wherein said processor is configured to evaluate a characteristic of said position shift and to also emit said signal indicative of a fault dependent on said characteristic.

11. A device as claimed in claim 9 wherein said processor is configured to emit a humanly-perceptible warning signal upon determination of said fault.

12. A device as claimed in claim 9 wherein said processor is configured to automatically preclude start-up of said hyperthermia applicator if said fault is determined to be present.

13. A device as claimed in claim 9 wherein said processor is configured to adapt a position of the focus of said hyperthermia applicator to the position-shifted location of the area to be treated.

14. A device as claimed in claim 9 wherein said processor is configured to determine a tissue region in said body region that comprises said area to be treated, and determine said position shift by comparing only data in said second image data representing said tissue region with only data in said first image data representing said tissue region.

15. A device as claimed in claim 9 wherein said processor is configured to determine said position shift by cross-correlating said first and second image data.

16. A device as claimed in claim 9 wherein said processor is configured to analyze said first and second image data to identify image sharpness information in each of said first and second image data, and determine said position shift dependent on the image sharpness information respectively in said first and second image data.

* * * * *